United States Patent [19]

Carter et al.

[11] 4,263,173

[45] Apr. 21, 1981

[54] SUPPORTED NICKEL-COBALT-SILICA COPRECIPITATED HYDROGENATION CATALYST

[75] Inventors: James L. Carter; Allan E. Barnett, both of Westfield; John H. Sinfelt, Berkeley Heights, all of N.J.

[73] Assignee: Exxon Research & Engineering Co., Florham Park, N.J.

[21] Appl. No.: 513

[22] Filed: Jan. 2, 1979

[51] Int. Cl.$^3$ .................. B01J 20/10; B01J 23/70; B01J 21/00

[52] U.S. Cl. .................. 252/452; 252/454; 252/455 R; 252/459

[58] Field of Search .................. 252/452, 454, 455 R, 252/459

[56] References Cited

U.S. PATENT DOCUMENTS

| | | | |
|---|---|---|---|
| 1,665,264 | 4/1928 | Holmes et al. | 252/452 |
| 1,815,790 | 7/1931 | Marx et al. | 252/459 |
| 2,759,023 | 8/1956 | Kool et al. | 252/459 |
| 3,087,966 | 4/1963 | Currier et al. | 252/459 X |
| 3,351,566 | 11/1967 | Taylor et al. | 252/452 |
| 3,547,830 | 12/1970 | Shropshire | 252/432 |
| 3,697,445 | 10/1972 | Carter | 252/452 |
| 3,945,944 | 3/1976 | Kang | 252/455 R |
| 4,088,603 | 5/1978 | Carter et al. | 252/459 X |
| 4,113,658 | 9/1978 | Geus | 252/454 |
| 4,184,982 | 1/1980 | Schroeder et al. | 252/452 |

FOREIGN PATENT DOCUMENTS 1000829 8/1965 United Kingdom .
1182929 3/1970 United Kingdom .

Primary Examiner—Carl F. Dees
Attorney, Agent, or Firm—Albert P. Halluin

[57] ABSTRACT

Supported coprecipitated nickel-cobalt-silica and nickel-cobalt-copper-silica hydrogenation catalysts are disclosed. The catalysts are prepared by preparing an aqueous reaction mixture containing nickel and cobalt cations (and optionally copper cations), silicate anions and solid porous carrier particles under agitation to form a coprecipitate of the nickel, cobalt (and optionally copper) and silicate ions onto said solid porous support particles; heating the aqueous reaction mixture; and adding an alkaline precipitating agent to further precipitate the nickel, cobalt (and optionally copper) and silicate anions onto said solid porous carrier particles.

24 Claims, No Drawings

4,263,173

SUPPORTED NICKEL-COBALT-SILICA COPRECIPITATED HYDROGENATION CATALYST

BACKGROUND OF THE INVENTION

1. Field of the Invention

This invention relates to coprecipitated nickel-cobalt-silica and nickel-cobalt-copper-silica hyrogenation catalysts and their use in hydrogenating organic compounds. In one aspect, this invention relates to the preparation of supported, coprecipitated nickel-cobalt-silica and nickel-cobalt-copper-silica catalysts. In another aspect, this invention relates to the use of the catalysts, in reduced form, to hydrogenate organic compounds.

2. Description of the Prior Art

The catalytic reduction of organic compounds in the presence of nickel and cobalt as well as nickel-cobalt or nickel-cobalt-copper catalysts is known. Nickel catalysts, especially supported nickel catalysts, have many commercial uses. For example, U.S. Pat. No. 3,535,271 teaches the use of a nickel catalyst promoted by copper for dehydrogenation, cracking, reforming, polymerization, isomerization, alkylation, as well as other treating processes. Other examples of nickel catalysts and their use in reforming and other processes include U.S. Pat. Nos. 2,750,261; 3,205,182; 3,351,566; 3,417,029; 3,697,445; 3,859,370; 3,868,332; 4,088,603; and Belgium Pat. No. 841,812 (which generally corresponds to U.S. application Ser. No. 577,328). In all of these patents, the catalysts are prepared by coprecipitation or impregnation processes wherein the catalytic metal precursors are either precipitated from solution in the presence of a support material or solution containing said precursor or impregnated into the pores of a porous support material. In British Pat. No. 1,220,105, for example, aqueous solutions are employed in conjunction with a homogeneous precipitation procedure to give highly dispersed nickel catalyst.

D. J. C. Yates, W. F. Taylor and J. H. Sinfelt (J. Am. Chem. Soc., 86, 2996 (1964)) described a chemisorption technique and its utility in correlating nickel particle size (and/or nickel surface area) with catalytic activity. In FIG. 3 of their publication, there is shown that a direct relation exists between reduced nickel surface area ($m^2$/g of catalyst) and initial reaction rate for ethane catalytically converted into methane (as mmoles $C_2H_6$ converted per hour per gram of catalyst). It follows, then, that methods which increase the nickel surface area of a nickel catalyst (other factors such as nickel content remaining constant) is a desirable feature, leading to a catalyst of improved catalytic activity. Patentees of U.S. Pat. Nos. 3,697,445; 3,859,370 and 3,868,332 also appreciated that achieving a higher degree of dispersion of nickel in the catalyst results in a more active catalyst and indeed they obtain a fairly high degree of dispersion by their coprecipitation techniques wherein nickel cations were gradually precipitated from an aqueous solution in the presence of silicate anion and solid porous particles to obtain dispersion greater than 70 $m^2$/g of reduced nickel metal per gram of catalyst. Belgium Pat. No. 841,812 teaches that the addition of copper ions during the precipitation step provides a catalyst that can be reduced at temperatures of approximately 200° C. U.S. Pat. No. 4,088,603 discloses an improved method of activating the coprecipitated nickel-copper-silica catalysts by gradually contacting the catalyst with a hydrocarbon feed and hydrogen.

A number of patents have disclosed cobalt, nickel-cobalt and nickel-cobalt-copper catalysts, e.g., U.S. Pat. Nos. 3,166,491; 3,385,670; 3,432,443; 3,547,830; 3,650,713; 3,661,798; 3,945,944; 4,014,933 and 4,026,823; and British Pat. Nos. 1,000,828; 1,000,829; 1,095,996; 1,095,987 and 1,182,829. None of these patents, however, disclose coprecipitation of silicate ions in conjunction with nickel and cobalt or nickel, cobalt and copper ions in the presence of solid porous carrier particles.

In some of the above-mentioned patents, for example, U.S. Pat. Nos. 3,697,445; 3,859,370; 3,868,332 and Belgium Pat. No. 841,812 it is mentioned that cobalt or iron may be used in place of nickel in the coprecipitation process. However, these patents only show nickel in the examples as the non-noble Group VIII catalytic metal used.

DISCOVERY OF THE PRESENT INVENTION

It has been discovered that, contrary to the suggestions in the aforementioned prior art, the non-noble Group VIII metals are not equivalent in terms of their catalytic hydrogenation properties when prepared by coprecipitation in the presence of silicate anions and solid carrier particles. In this connection, it has been found that when nickel is replaced by iron in the process of U.S. Pat. No. 3,697,445, the resulting calcined and reduced catalyst does not appreciably catalyze the hydrogenation of benzene to cyclohexane while the initial argon B.E.T. surface area of the catalyst was 256 $m^2$/g. However, quite surprisingly, when a portion of the nickel is replaced by cobalt in the catalyst prepared in accordance with the teachings in U.S. Pat. No. 3,697,445, the resulting catalyst, following reduction at 75°–400° C., has a higher catalytic hydrogenation activity, particularly at certain hereinafter specified ratios of cobalt to nickel. The hydrogenation activity of certain coprecipitated nickel-cobalt-silica catalysts is higher than anticipated. Surprisingly, the supported coprecipitated nickel-cobalt-silica catalyst which additionally contains coprecipitated copper, has substantially more hydrogenation activity than the coprecipitated nickel-copper-silica catalyst of Belgium Pat. No. 841,812 and this new coprecipitated nickel-cobalt-copper-silica catalyst surprisingly has a greater hydrogenation activity when reduced at temperatures ranging from 195° to 225° C. than at 400° C.

SUMMARY OF THE INVENTION

In one embodiment of the invention, there is provided a supported nickel-cobalt-silica coprecipitated hydrogenation catalyst characterized as having a B.E.T. total surface area ranging from about 150 to about 350 $m^2$/g wherein the nickel to cobalt ratio in the catalyst ranges from about 63 to about 0.3, or the nickel to cobalt ratio ranges from about 0.067 to about 0.017 and the total amount of nickel plus cobalt in the calcined and reduced catalyst ranges from about 25% to about 70 wt. %. The catalyst of the present invention may additionally include copper, preferably coprecipitated with the nickel and cobalt in an amount ranging from about 1 wt. % to about 10 wt. % based on the weight of the catalyst. The presence of the copper serves to facilitate reduction of the catalyst at lower temperatures and provides a catalyst having a greater hydrogenation activity when reduced at the lower temperatures.

In another embodiment of the invention, there is provided a process for preparing a supported coprecipitated nickel-cobalt-silica hydrogenation catalyst comprising the steps:

(a) preparing a reaction mixture comprising an aqueous solution containing nickel, cobalt and silicate ions and solid porous carrier particles under agitation to form a precipitate of the nickel, cobalt and silicate ions onto said solid porous support particles;

(b) heating the aqueous reaction mixture; and (c) adding an alkaline precipitating agent to further precipitate the nickel, cobalt and silicate ions onto said solid porous support particles.

The nickel, cobalt, silicate ions and solid porous carrier particles are present in proportions sufficient to provide a nickel to cobalt ratio in the catalyst that ranges from about 63 to about 0.3, or the nickel to cobalt ratio ranges from about 0.067 to about 0.017.

In this process, copper ions may be added to the aqueous reaction mixture, in an amount sufficient to provide from about 1 wt. % to about 10 wt. % of copper in the catalyst, the weight percent being based on a total weight of the catalyst. The total amount of Group VIII metals in the catalyst, i.e., cobalt and nickel will generally range from about 25 to about 70 wt. % based on the weight of the calcined and reduced catalyst. Following preparation of the catalyst, the catalyst is washed, and thereafter the catalyst may be calcined under oxidative conditions at a temperature ranging from about 300° to about 450° C. and reduced in the presence of a reductant at temperatures ranging from about 75° C. to 400° C. The final catalyst preparation, for use in hydrogenation processes preferably contains less than 0.1 wt. % sodium, based on the total weight of the catalyst.

In still another embodiment of the present invention, there is provided a process for hydrogenating organic compounds, which comprises contacting at least one hydrogenatable organic compound with a reducing agent such as hydrogen in the presence of the hereinabove described catalyst preparation in its calcined and reduced state. Typical organic compounds which may be reduced by the process of the invention include aromatic compounds such as benzene, olefins, aldehydes and nitriles.

DESCRIPTION OF THE PREFERRED EMBODIMENT

As generally discussed above, the catalysts of the present invention are prepared by preparing a reaction mixture comprising an aqueous solution containing nickel and cobalt cations (which may optionally include together or separately cooper cations), silicate anions and solid porous carrier particles as the support material such as kiesulguhr. Preferably a solution containing the Group VIII metal cations is uniformly comingled with the silicate anion solution, with solid porous carrier particles slurried therein, by the addition of the cation-containing solution to the support containing silicate solution over a period of approximately 5 to 40 minutes. Alternatively, the solution containing silicate ions may be added to the solution of nickel and cobalt cations with the solid porous support particles slurried therein. By comingling the previously prepared solutions, the amount of dissolved metal ions (nickel and cobalt ions) in the reaction mixture may be controlled; preferably it will be below 0.60 moles/liter of the aqueous reaction mixture. This dilution of the dissolved nickel and cobalt ions is preferred in obtaining a high catalytic activity. Also, the addition should be made at a substantially constant rate accompanied by vigorous mixing to increase uniformity in the catalyst formation. The mixture is then heated, preferably up to its boiling point at atmospheric pressure, and a precipitating agent is added to coprecipitate the remaining dissolved, silicate and metallic ions onto the porous support particles.

During catalyst preparation, water is added to the reaction mixture to maintain a nearly constant volume so that water loss by evaporation is continually replaced. The aqueous reaction mixture is preferably kept at its boiling point (at atmospheric pressure) for a period of one to five hours; (although heating at a temperature below the boiling point of the solution, i.e., 60° to 99° C. may be employed to minimize evaporation); it is then filtered and the resulting product is washed repeatedly with boiling water to remove alkali metals and other impurities. (Generally, the washings will be four or more times). Then, the catalyst is dried at temperatures ranging from 90°–200° C. for one to five hours and calcined in an oxygen source, e.g., an oxygen-containing gas such as air to a temperature ranging from 300°–450° C. for a period of 2–8 hours, preferably 3–5 hours. The finished catalyst can then be charged directly (or subsequent to shaping or extruding such as in the form of tablets or pellets) into the reaction vessel, without activation, and activated in the reaction vessel with a gaseous reductant, usually flowing hydrogen.

As stated previously, the nickel and cobalt containing solution and the silicate-containing solution are preferably comingled under conditions of dilution such that the amount of dissolved cobalt and nickel ions in the resultant reaction mixture is maintained exceedingly low thereby providing for a high catalytic activity. Additionally, however, it is preferred that in preparing the catalyst of this invention, that the coprecipitation of the catalyst is made from dilute solutions, i.e., the nickel-cobalt-containing solutions should have a metal (nickel and cobalt) concentration no greater than 1.0 moles/liter and the other solution a silicate ion (e.g., alkali-metal metasilicate) concentration no greater than 0.4 moles/liter. When copper cations are included in the reaction mixture, the copper concentration is determined by the desired amount of copper in the catalyst. The preferred solution used in preparing the catalyst has no more than 0.75 moles/liter of metal ions (cobalt and nickel ions), more preferably less than 0.6 moles/liter and 0.26 moles/liter of silicate ions, e.g., sodium metasilicate. This is contrasted with a more concentrated precipitation in which the solution contains up to twice as much solute. The mole ratio of metal (cobalt and nickel) to silicate employed ranges from about 0.3:1 to about 2.5:1 in the calcined and reduced catalyst.

In the case of the silicate-porous silica based catalysts about 30 to 90 wt.% of the total silica content of the activated catalyst is derived from precipitated silicate ions when the solid porous particles are comprised of silica, e.g., kieselguhr. Preferably, however, 50 to 70 wt. % of the total silica content is derived from the silicate ions when the solid porous particles are comprised of silica.

The remaining steps in preparing and activating the catalyst are identical to those described above.

In a preferred aspect of the invention the catalyst of the invention is formed by coprecipitating nickel and cobalt (and optionally including copper) and silicate ions onto a solid porous particulate support preferably solid porous silica particles from an aqueous solution. In this preferred embodiment of the invention, two distinct solutions are prepared with solid porous particles slurried in one of them. In one of these solutions is a silicate ion source such as alkali metal silicates, i.e., sodium and potassium silicates, sodium metasilicate, etc. or salicic acid ion source which is preferably slurried in an aqueous mixture containing solid porous particles.

A second solution, containing a source of nickel and cobalt cations (and optionally copper cations) is also prepared; the source of the nickel and cobalt cations may be any of the following: nickel and cobaltous nitrate, nickel chloride, nickel bromide, cobaltous chloride and cobaltous bromide. The source of the copper cation may be also copper nitrate, copper chloride and copper bromide.

Other sources of nickel, cobalt and copper cations and silicate anions may be utilized and may be obvious to one skilled in the art. The salts of the metal are the water-soluble compounds, e.g., nitrates, halides, formates or oxalates.

As discussed above, the solid porous particles, preferably silica particles, will be slurried in either the silicate anion solution or the nickel/cobalt containing solution. In particular, kieselguhr, infusorial earth, diatomaceous earth, siliceous earth, silica or alumina will be the source of the porous particles. The concentration of the solid porous particles can be expressed as percent of total silica in the catalyst and should be from 10 to 70 wt. %, preferably from 30 to 50 wt. %, i.e., when the solid porous particles are silica-based.

The solution containing the metal cation(s) and the other solution containing the silicate anions with one containing the solid porous particles, are comingled at a slow rate to effect maximum mixing. Typically, the nickel and cobalt (which may optionally include copper ions) solution would be added to a sodium metasilicate solution, with kieselguhr slurred therein, uniformly over approximately a 5 to 40 minute period, preferably 10 to 30 minute period. Alternatively the solution containing the sodium metasilicate may be added to the nickel/cobalt solution, which has the solid porous particles slurried therein. The mixture is then heated. Coprecipitation is completed by various methods known in the art, but it is most preferred that the coprecipitation of the nickel and cobalt (and optionally with the addition of copper) and silicate ions in the aqueous solution containing the solid porous particles be completed by the addition of a water soluble alkaline precipitating agent. The alkaline ammonium precipitants are most suitable for minimizing the amount of alkali metal residue which has to be removed by washing to avoid poisoning action on the finished catalyst. In some instances, the potassium precipitants may be used where the potassium acts as a promoter rather than a poison. Sodium carbonate is still another example of a suitable water soluble alkaline precipitating compound. Various organic alkaline materials may be used to complete the precipitation such as urea, primary and secondary amines. However, a preferred precipitating agent is ammonium bicarbonate.

The precipitated catalyst is preferably washed to remove impurities, particularly sodium. If it is desired to remove the trace levels of sodium in the catalyst, one may wash the filter cake with a washing liquor comprising a mixture of water and a small amount, i.e., about 100 ppm of a filtering aid such as sodium or potassium carbonate or nitrate or 200 ppm of ammonium carbonate. In this connection reference is made to U.S. Pat. No. 4,105,591, the disclosure of which is incorporated by reference.

After the washing, drying and calcining of the catalyst is completed, the catalyst must be reduced in order to activate it. Reduction is carried out in the presence of a reductant such as a reducing gas which is preferably hydrogen. The reducing gas is passed over the catalyst at ambient temperature at a rate of 5 l/hr/gm to 30 l/hr/gm and then the temperature is raised to a range of from 75° C. to 400° C. In the case of the coprecipitated nickel-cobalt-copper-silica catalyst of the invention lower temperatures of reduction may be employed, i.e., from 150° to about 350° C., preferably from 175° C. to about 250° C. and more preferably from about 195° to about 225° C. Unexpectedly, the coprecipitated nickel-cobalt-copper-silica catalyst has a higher hydrogenation catalytic activity at the lower reduction temperature range, i.e., 195° to 225° C. than at the higher reduction temperatures, i.e., 400° C.

The reduction (activation) is preferably carried out after the catalyst has been loaded into the reaction vessel (in the case of the cobalt-nickel-copper-silica containing catalyst) where the hydrogenation will be carried out, which may be either batch or continuous. The nature of the reactor will be obvious to one skilled in the art. The activation procedure of U.S. Pat. No. 4,088,603 may be used with the catalyst of the present invention.

The activated catalyst is sensitive to deactivation and may not be stored in the presence of oxygen at ordinary temperatures without first being passivated. The passivation step may consist of purging the reactor at a temperature greater than 300° F. with an inert gas, preferably nitrogen, cooling to ambient temperature and then passing the inert gas so as to have approximately 1-2 mol percent oxygen present. This procedure will passivate the catalyst by putting a surface oxide coating on it. Preferably, the catalyst will be passivated by the process of U.S. Pat. No. 4,090,980, the disclosure of which is incorporated herein by reference.

The B.E.T. total surface area of the catalyst of the invention will generally range from about 150 to about 350 $m^2/g$, preferably 225 $m^2/g$ to about 325 $m^2/g$. The method for measuring the total catalyst surface area known as the B.E.T. method is described in Emmett, P.H., *Advances in Catalysis*, I, 65 (1948). Also, the catalyst preferably contains about 0.1 wt. % or less of sodium.

The catalysts of the instant invention are useful in hydrogenating hydrogenatable organic compounds. In this connection the catalysts of the instant invention may be used to hydrogenate aromatic containing compounds as typified by the hydrogenation of benzene to cyclohexane, the hydrogenation of aldehydes, both saturated and unsaturated to the alcohols as in the well-known oxo process, the hydrogenation of the double bonds in edible fats and oils as well as other olefins both straight and branched chain, the hydrogenation of aromatics in white oil base stock to produce high grade white oil, the hydrogenation of nitro compounds to amines and the hydrogenation of nitriles to amines. Indeed, olefins as used herein signify unsaturated compounds having at least one multiple bond and contemplates polyunsaturated compounds as well.

The conditions for the hydrogenation reactions have been discussed very widely and are well-known to those skilled in the art; broadly the following conditions may be utilized: temperatures ranging from about 25° C.

to 300° C., preferably from 75° C. to 250° C; pressures ranging from 1 atmosphere to 800 atmospheres, preferably from 1 atmosphere to 50 atmospheres; feed rates of from 0.2 to 100 volumes per hour per volume of catalyst and hydrogen addition of from 500 to 10,000 standard cubic feet per barrel (SCF/B) of feed may be used.

In the case of the oxo process, i.e., the addition of carbon monoxide and hydrogen to alkene to produce alcohols, aldehydes and other oxygenated organic compounds, one would typically employ conditions such that the temperatures would range from about 70° C. to 175° C. and use a hydrogen to hydrocarbon mole ratio of 0.5 to 10 and a pressure of 100 to 1000 psig. The alkenes used in such a process would typically contain 2 to 20 carbon atoms. The product of such a carbonylation process generally consists of aldehydes, acetals, unsaturated oxygenated materials and the like which require hydrofinishing in a second or further hydrogenation stage. It is to the treatment of the aldehyde product, in particular, that the present invention applies. Hydrogenation conditions in this further reaction stage follow those generally employed in the first stage.

Another useful improved hydrogenation is the conversion of aromatics in white spirits to yield high quality solvents. The upgrading of white spirits by the process of the instant invention is an improvement in the treatment of such materials.

Still another useful improved hydrogenation of the invention is the conversion of olefins in paraffin solvents such as denonenizer bottoms and deoctenizer overheads.

Two especially useful hydrogenation processes included within the scope of the invention include the hydrogenation of aromatics such as benzene to cyclohexane and the production of amines from nitro compounds and nitriles. For example, the invention is useful in converting $C_{12}$ to $C_{24}$ nitriles to the corresponding fatty acid amines. Also, aromatic nitro compounds may be converted to amines, e.g., nitrobenzene to aniline or the conversion of aromatic amines to cycloaliphatic amines, e.g., aniline to cyclohexyl amine.

The following examples serve to more fully describe the manner of making and using the above-described invention, as well as to set forth the best modes contemplated for carrying out various aspects of the invention. It is understood that these examples in no way serve to limit the true scope of this invention, but rather, are presented for illustrative purposes.

A specific procedure for preparing the preferred catalysts having a nickel to cobalt ratio of 9:1 is as follows:

An aqueous premix containing 1518 g. Ni(NO$_3$)$_2$.6H$_2$O, 169 g. Co(NO$_3$)$_2$.6H$_2$O and 113 g. Cu(NO$_3$)$_2$.3H$_2$O dissolved in 7.5 liters of distilled water or low sodium ion water is prepared as a first solution. A second aqueous solution is prepared containing 570 g. Na$_2$SiO$_3$.9H$_2$O dissolved in another 7.5 liters of distilled water or low sodium ions water and 75 g. kieselguhr (Celite F.C. or Hyflow A.W.—Johns Manville or equivalent) is slurried in the solution thereafter. The first solution is then slowly added to the second solution (slow addition is employed to avoid localized high concentrations) while stirring vigorously until all of the nitrate solution has been added. The mixture is then heated to near the boiling point and stirring is continued while adding 1608 g. Na$_2$CO$_3$ slowly, to avoid the too rapid evolution of CO$_2$ gas. The mixture is kept at the boiling point for a total of about 3 hours after the addition of Na$_2$CO$_3$ while stirring is continued. The slurry is then washed continuously with low-sodium ion water to remove most of the sodium ion. Then the slurry is spray-dried. The spray-dried powder is then washed sufficiently to obtain a sodium content in the finished catalyst of less than 0.1 wt. %. Alternately, if the required low sodium content can be attained during the previous washing step then it would not be necessary to wash the spray-dried powder. The powder is then dried at 220° F. (105° C.) to less than 2.5 wt. % water (loss on drying at 300° F. (165° C.) for 3 hours). The powder is then formed into pills or preferably extrudates of suitable crush strength. The ⅛"×⅛" pills typically will have a crush strength greater than 7 pounds. Graphite or a similar lubricant may be used in the customary manner as a pilling aid. The pills are then calcined in a rotary calciner at a maximum temperature of about 750° F. (400° C.). It is important to avoid driving off water at high temperatures ("steaming" the catalyst), and a heat-up time sufficient to eliminate all moisture before the pills enter the high temperature zone must be provided. Therefore, a temperature gradient from about 250° F. (121.1° C.) at the catalyst inlet to 750° F. (398.8° C.) at the catalyst outlet with a residence time of at least one hour at 750° F. is required. Maximum air flow should be used with the direction of flow from the catalyst outlet to inlet.

In order to prepare a catalyst having a nickel to cobalt ratio of 1:9 the same procedure is followed except that the first solution contains 169 g. Ni(NO$_3$)$_2$.6H$_2$O, 1518 g. Co(NO$_3$)$_2$.6H$_2$O and 113 g. Cu(NO$_3$)$_2$.3H$_2$O.

Each of the catalyst preparations will contain about 45 wt. % of nickel plus cobalt, about 5 wt. % copper and about 50 wt. % SiO$_2$.

EXAMPLE 1

A coprecipitated nickel-cobalt-silica catalyst was prepared in the following manner: In 500 ml of distilled water there was dissolved 3.16 g of Co(NO$_3$)$_2$.6H$_2$O and 59.78 g of Ni(NO$_3$)$_2$.6H$_2$O. Then 2.8 g of kieselguhr was slurried in the metal salt solution. In another 125 ml of distilled water there was dissolved 21.25 g of Na$_2$SiO$_3$.9H$_2$O. This solution was added dropwise over a 15 to 20 minute period into the first metal salt solution as it was being rapidly stirred. The resulting mixture was heated to above 80° C. and 42.4 g of NH$_4$HCO$_3$ was added; the solution was thoroughly mixed for another 30 minutes. The coprecipitated catalyst was then filtered and the filter cake was washed four times by re-slurrying in one liter of water. The filter cake was again filtered and the cake was dried at 110° C. and calcined in air for 2 hours at 400° C.

The above procedure was repeated several times keeping the total metal content constant at 64 wt. %, based on the weight of the calcined and reduced catalyst, but varying the amounts of Co(NO$_3$)$_2$.6H$_2$O and Ni(NO$_3$)$_2$.6H$_2$O to vary the cobalt to nickel ratios. Each of the catalysts prepared was reduced with hydrogen at 400° C. for 16 hours and used to hydrogenate benzene to cyclohexane to ascertain their relative hydrogenation catalytic capabilities. The results of these experiments are shown in Table I.

TABLE I

| CATALYTIC CONVERSION OF BENZENE TO CYCLOHEXANE[a] | |
|---|---|
| Ni/Co Ratio[b] | Benzene Conversion, % |
| 100% Ni | 57 |

TABLE I-continued

CATALYTIC CONVERSION OF BENZENE TO CYCLOHEXANE[a]

| Ni/Co Ratio[b] | Benzene Conversion, % |
|---|---|
| 19 | 72 |
| 9 | 80 |
| 4 | 87 |
| 2.3 | 81 |
| 1 | 73 |
| .43 | 74 |
| .25 | 51 |
| .11 | 55 |
| .05 | 82 |
| 100% Co | 87 |

[a]Reaction Conditions: 1 atmosphere; Temperature: 78° C.; Feed: 90% n-hexane, 10% benzene; Feed rate: 53 W./Hr./W., 5.8 moles $H_2$/mole hydrocarbon; Catalyst charge: 0.25 gm.
[b]Based on the amount of nickel and cobalt in the coprecipitated catalyst after calcination and reduction.

EXAMPLE 2

To further illustrate the invention four activated catalyst preparations were prepared by the coprecipition procedure of Example 1 wherein the coprecipitated catalyst had a nickel to cobalt ratio of 9:1. The first catalyst preparation was reduced at 400° C. for 16 hours, the second and third catalyst preparations were impregnated with 1% copper and reduced at 400° C. and 200° C., respectively and the fourth catalyst preparation contained 5 wt. % copper coprecipitated into the catalyst. The fourth catalyst preparation was reduced at 200° C. for 16 hours. Each of the catalysts was used to hydrogenate benzene to cyclohexane to ascertain their relative hydrogenation catalytic capabilities. The results of these experiments are shown in Table II.

TABLE II

CATALYTIC CONVERSION OF BENZENE TO CYCLOHEXANE[a]

| $\frac{9\ Ni}{1\ Co}$ / $SiO_2$[b] | | $\frac{9\ Ni}{1\ Co}$ / $SiO_2$[c] Impregnated with 1 wt. % Cu | | $\frac{9\ Ni}{1\ Co}$ / $SiO_2$[d] Impregnated with 1 wt. % Cu | | $\frac{9\ Ni}{1\ Co}$ / $SiO_2$[e] Coprecipitated with 5 wt. % Cu | |
|---|---|---|---|---|---|---|---|
| Time (Hr.) | Benzene Conversion % | Time (Hr.) | Benzene Conversion % | Time (Hr.) | Benzene Conversion % | Time (Hr.) | Benzene Conversion % |
| 0.3 | 84.4 | 0.25 | 69.9 | 0.5 | 93.3 | 0.5 | 99 |
| 1 | 82.8 | 1 | 69.4 | 1 | 91.7 | 1 | 99 |
| | | 2 | 66.2 | 2 | 90.9 | 2 | 99 |
| 3 | 80.1 | 3 | 66.0 | 3 | 89.9 | 3 | 99 |
| 4 | 79.8 | 4 | 64.0 | 4 | 90.0 | 4 | 98.3 |

[a]Reaction Conditions: 1 atmosphere; Temperature: 78° C.; Feed: 90% n-hexane, 10% benzene; Feed rate: 53 W./Hr./W.; 5.8 moles $H_2$/mol hydrocarbon; Catalyst Charge: 0.25 gm.
[b]Catalyst reduced at 400° C. for 16 hrs. (The catalyst had a B.E.T. total surface area of 231 $m^2$/g).
[c]Catalyst reduced at 400° C. for 16 hrs.
[d]Catalyst reduced at 200° C. for 16 hrs.
[e]Catalyst reduced at 200° C. for 16 hrs. (The catalyst had a B.E.T. total surface area of 246 $m^2$/g).

The results in Table II clearly demonstrate that coprecipitating copper in the cobalt-nickel-silica catalyst of the invention, coupled with low temperature reduction, produces a catalyst having extraordinary hydrogenation activity for converting benzene to cyclohexane. This is an unexpected result since lowering the reduction temperature below 400° C. generally reduces the catalytic activity in nickel and nickel-copper coprecipitated hydrogenation catalysts.

EXAMPLE 3

For the purposes of comparison an iron containing catalyst was prepared in the following manner: 91.2 gm of $Fe(NO_3)_3.9H_2O$ was dissolved in 500 ml of distilled water. To this solution there was added 2.8 gm of kieselguhr followed by the addition under conditions of vigorous mixing 200 ml of an aqueous solution containing 21.26 gm of $Na_2SiO_3.9H_2O$. Mixing of this comingled solution was continued and followed by heating to about 80° C. The coprecipitation was completed by the addition of 67.2 gm of ammonium bicarbonate. The mixture was mixed for an additional 30 minutes after the last addition, and diluted to 4 liters with water, washed by decantation 2 times with 4 liter washes, filtered and dried at 120° C. The catalyst was calcined for 3 hours at 400° C. The catalyst had an argon B.E.T. total surface area after evacuation at 260° C. of 256 $m^2$g. After overnight reduction at 400° C., the catalyst had a metal surface determined by hydrogen chemisorption to be less than one $m^2$/g catalyst, and an argon B.E.T. surface area of only 132 $m^2$/g of catalyst.

An attempt was made to convert benzene to cyclohexane using the iron catalyst prepared above. The reaction conditions were as follows: Pressure 1 atm; Temperature: 76°-77° C.; Feed: 90% N-hexane, 10% benzene; Feed rate: 20 cc/hr; $H_2$ rate: 20.4 liters/hour; Catalyst charge: 0.25 gms of catalyst which had been reduced 16 hours at 400° C. Samples of product were taken at 15 minutes, 30 minutes and 60 minutes and there was no sign of benzene conversion in any of these samples. The temperature was raised to 112° C. and the product was sampled to find no conversion of benzene to cyclohexane.

The above tests demonstrate that the non-noble metal silica coprecipitated compositions, i.e., nickel, cobalt and iron are not equivalent in their hydrogenation catalytic properties. The iron containing composite prepared by the process of U.S. Pat. No. 3,697,445 had substantially no detectable catalytic activity with respect to converting benzene to cyclohexane, whereas nickel and cobalt containing catalysts have good hydrogenation catalytic activity. Unexpectedly the cobalt-nickel-silica and particularly the cobalt-nickel-copper-silica catalysts of the present invention have especially improved hydrogenation catalytic activity.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A calcined and supported coprecipitated nickel-cobalt-silica catalyst characterized as having a B.E.T.

total surface area ranging from about 150 to about 350 m²/g wherein the nickel to cobalt ratio in the catalyst ranges from about 63 to about 0.3 or the nickel to cobalt ratio ranges from about 0.067 to about 0.017 and the total amount of the cobalt and nickel in the catalyst ranges from about 25 wt. % to about 70 wt. % based on the total weight of the calcined and reduced catalyst, wherein said catalyst has been prepared by coprecipitating cobalt, nickel and silicate ions onto solid porous particles.

2. The catalyst in accordance with claim 1 wherein the catalyst contains about 0.1 wt. % or less sodium based on the total weight of the active catalyst.

3. The catalyst in accordance with claim 1 wherein the solid porous particles are selected from the group consisting of kieselguhr, infusorial earth, diatomaceous earth, siliceous earth, silica and alumina.

4. The catalyst in accordance with claim 3 wherein the porous solid particles are kieselguhr.

5. The catalyst in accordance with claim 4 which additionally includes coprecipitated copper in an amount ranging from 1 wt. % to about 10 wt. % based on the total weight of the catalyst.

6. The catalyst in accordance with claim 4 wherein the amount of porous solid particles ranges from about 10 wt. % to about 70 wt. % based on the total silica in the catalyst.

7. The catalyst in accordance with claim 6 wherein the amount of the porous solid particles ranges from 30 wt. % to about 50 wt. % based on the total silica in the catalyst.

8. The catalyst in accordance with claim 1 which has been reduced to an active state.

9. A calcined and supported coprecipitated nickel-cobalt-copper-silica catalyst characterized as having a B.E.T. total surface area ranging from about 225 to about 325 m²/g wherein the nickel to cobalt ratio in the catalyst ranges from about 63 to about 0.3, wherein the total amount of cobalt and nickel in the catalyst ranges from about 25 wt. % to about 70 wt. %, based on the total weight of the calcined and reduced catalyst, and the amount of copper in the catalyst ranges from about 1 wt. % to about 10 wt. %, said wt. % of copper being based on the total weight of the calcined and reduced catalyst, said catalyst being supported by porous solid particles comprising kieselguhr, wherein the amount of kieselguhr ranges from about 30 wt. % to about 50 wt. % based on the total silica in the catalyst.

10. The catalyst in accordance with claim 9 which has been reduced to an active state.

11. A process for preparing a calcined and supported coprecipitated nickel-cobalt-silica catalyst comprising the steps:
(a) preparing a reaction mixture containing cobalt, nickel and silicate ions and solid porous carrier particles to form a coprecipitate of the cobalt, nickel and silicate ions onto said solid porous support particles;
(b) heating the aqueous reaction mixture;
(c) adding an alkaline precipitating agent to further coprecipitate the cobalt, nickel and silicate ions onto said solid porous support particles wherein the cobalt, nickel, silicate ions and solid porous carrier particles are present in proportions sufficient to provide a nickel to cobalt ratio ranging from about 63 to about 0.3 or ranging from about 0.067 to about 0.017 and the total amount of cobalt and nickel in the catalyst ranges from about 25 to about 70 wt. % based on the total weight of the calcined and reduced catalyst; and
(d) drying said coprecipitated catalyst and calcining it at a temperature ranging from 300° to 450° C. under oxidative conditions.

12. The process of claim 11 wherein silicate ions are used in the precipitation step and the solid porous particles are selected from the group consisting of kieselguhr, infusorial earth, diatomaceous earth, siliceous earth, silica and alumina.

13. The process of claim 11 wherein copper ions are added to the comingled reaction mixture in an amount sufficient to provide from 1 wt. % to about 10 wt. % of copper in the catalyst, based on the total weight of the calcined and reduced catalyst.

14. The process of claim 11 wherein the precipitating agent is ammonium bicarbonate.

15. The process of claim 11 which additionally includes the step of reducing said catalyst at a temperature ranging from 75° C. to 400° C. in the presence of a reductant.

16. The catalyst produced by the process in accordance with claim 11.

17. A calcined and activated coprecipitated nickel-cobalt-silica catalyst of high activity for hydrogenation of reducible organic compounds, said catalyst being characterized as having a B.E.T. total surface area ranging from about 150 to about 350 m²/g, wherein the nickel to cobalt ratio in the catalyst ranges from about 63 to about 0.3 or the nickel to cobalt ratio ranges from about 0.067 to about 0.017 and the total amount of the cobalt and nickel in the catalyst ranges from about 25 wt. % to about 70 wt. % based on the total weight of the calcined and reduced catalyst, wherein said catalyst has been prepared by the process comprising:
(a) uniformly comingling a first aqueous solution containing silicate anions and solid porous carrier particles comprising kieselguhr with a second solution containing nickel and cobalt cations under conditions of dilution such that the total amount of dissolved nickel and cobalt cations in the comingled reaction solution is below 0.60 moles/liter;
(b) heating the comingled reaction mixture;
(c) adding a precipitating agent to coprecipitate the nickel, cobalt and silicate ions onto said solid porous carrier kieselguhr particles;
(d) drying said coprecipitated catalyst and calcining it at a temperature ranging from 300° to 450° C. under oxidative conditions; and
(e) reducing the calcined catalyst with a gaseous reductant at temperatures ranging from 75° C. to 400° C. until said catalyst has been at least partially activated by the reduction.

18. The catalyst in accordance with claim 17 which additionally includes coprecipitated copper in an amount ranging from 1 wt. % to about 10 wt. % based on the total weight of the catalyst.

19. The catalyst in accordance with claim 17 wherein the amount of porous solid particles ranges from about 10 wt. % to about 70 wt. % based on the total silica in the catalyst.

20. The catalyst in accordance with claim 19 wherein the amount of the porous solid particles ranges from 30 wt. % to about 50 wt. % based on the total silica in the catalyst.

21. The catalyst in accordance with claim 18 wherein the calcined catalyst has been reduced at temperatures ranging from about 150° to about 350° C.

22. The catalyst in accordance with claim 18 wherein the calcined catalyst has been reduced at temperatures ranging from about 170° to about 250° C.

23. The catalyst in accordance with claim 18 wherein the calcined catalyst has been reduced at temperatures ranging from about 195° to about 225° C.

24. The catalyst in accordance with any of claims 18, 19, 20, 21, 22, or 23, wherein the catalyst has been passivated.

* * * * *